United States Patent
Krahn et al.

[11] Patent Number: 6,114,863
[45] Date of Patent: Sep. 5, 2000

[54] METHOD FOR DETERMINING THE PRESENCE OF WATER IN MATERIALS

[75] Inventors: John Raymond Krahn, Schenectady; Clive William Reed, Scotia, both of N.Y.

[73] Assignee: General Electric Company, Schenectady, N.Y.

[21] Appl. No.: 09/069,448

[22] Filed: Apr. 29, 1998

[51] Int. Cl.[7] .......................... G01R 27/28; G01R 27/26; G01R 27/08

[52] U.S. Cl. .......................... 324/664; 324/673; 324/674; 324/694

[58] Field of Search .................... 324/544, 658, 324/663, 664, 667, 683, 689, 724, 674; 73/74, 664, 694

[56] References Cited

U.S. PATENT DOCUMENTS

| | | | |
|---|---|---|---|
| 3,766,471 | 10/1973 | Pullman | 324/65 R |
| 3,870,951 | 3/1975 | Brown et al. | 324/61 P |
| 3,940,754 | 2/1976 | Weber . | |
| 3,966,973 | 6/1976 | Henry et al. . | |
| 4,352,059 | 9/1982 | Suh et al. | 324/61 R |
| 4,468,611 | 8/1984 | Tward | 324/61 R |
| 4,522,060 | 6/1985 | Murata et al. . | |
| 4,658,207 | 4/1987 | Scribano et al. | 324/61 R |
| 5,134,380 | 7/1992 | Jonas | 324/674 |
| 5,283,711 | 2/1994 | Schmitz | 361/286 |
| 5,345,821 | 9/1994 | Reich et al. | 73/335.04 |
| 5,442,293 | 8/1995 | Lange | 324/332 |
| 5,859,536 | 1/1999 | Stockton | 324/664 |

FOREIGN PATENT DOCUMENTS

| | | |
|---|---|---|
| 2298923 | 9/1996 | United Kingdom . |
| 9628741 | 9/1996 | WIPO . |

OTHER PUBLICATIONS

Derwent Abstract AN 93–204433, Jun. 30, 1992.

European Search Report.

AF Friedeck, "Detecting and Locating Stator Cooling–Water Leaks", Rotating Machinery, Doble Engineering Company, 60AIC93, 1993, pp. 7–9.1–7–9.10.

Viktor Kogan et al., "On Line Water Leakage Detection System In Water Cooled Generator Stator Windings", EPRI Workshop, Atlanta, GA, Maintaining The Integrity of Water–Cooled Generator Stator Windings, held Jun. 1995, pp. 1–20.

JE Timperley, "Capacitance Mapping Of A Series Connection With An Active Water Leak", Rotating Machinery, Doble Engineering Company, 62PA1C95, 1995, pp. 7–5.1–7–5.5 and "Discussion of James E. Timperley Paper", 7–5A.1–7–5A.3.

H. Gonishi et al., "Development of New Diagnostic Method For Hot–Line XLPE Cables With Water Trees", IEEE Transactions on Power Delivery, vol. PWRD–2, No. 1, Jan. 1987.

(List continued on next page.)

*Primary Examiner*—Safet Metjahic
*Assistant Examiner*—James C Kerveros
*Attorney, Agent, or Firm*—Donald S. Ingraham; Douglas E. Stoner

[57] ABSTRACT

An improved process for determining the presence of water in a material is disclosed. A set of electrodes is placed on the surface of a layer of the material being monitored, and an electric field is established therebetween. The phase angle for the electric field at a pre-selected frequency is measured, and compared with a predetermined phase angle for a dry portion of the material. A significant difference between the phase angle for the material being monitored and the predetermined phase angle is indicative of the presence of water in the material. The material being monitored may be an electrical insulating material, e.g., for conductive components in water-cooled electrical generators. Electrical generators monitored in this manner are also within the scope of this disclosure.

33 Claims, 2 Drawing Sheets

OTHER PUBLICATIONS

Richard C. Arbour et al., Diagnosing High–Potential Test Failures in Large Water–Cooled Hydrogenerators Bureau of Reclamation, PO Box 25007, Denver Federal Center, Denver, CO 80225, pp. 228–235.

"Inspection of Generators with Water Cooled Stator Windings", General Electric Technical Information Letter, GE Power Generation, TIL 1098–3R2, Jan. 24, 1995, pp. 1–8.

NV Afanas'ev et al., "The Effect of Film Water On The Dielectric Properties of Mica—Part I", from Researchy In Surface Forces, vol. 2, pp. 176–180, NV Derjaguin, Ed. (1966), Consultants Bureau, NY.

J. Timperley, in *Rotating Machinery*, 62 PAIC 95 (p. 3 specification), Missing Date.

H. Oonishi et al., IEEE Transactions on Power Delivery, vol. PWRD–2, No. 1, Jan. 1987, (p. 5 of the specification).

"Structure of Water Near Solid Interfaces", Industrial and Engineering Chemistry, vol. 61, No. 11, Nov. 1969, pp. 10–47 (p. 8 of the specfication).

*Kirk–Othmer Encyclopedia of Chemical Technology*, 3rd Edition, vol. 18, (1982) (p. 9 of the specification).

"Motions and Relaxations of Combined Liquids", S. Granick, *Science*, vol. 253, Sep. 1991, pp. 1374–1379 (p. 9 of the specification).

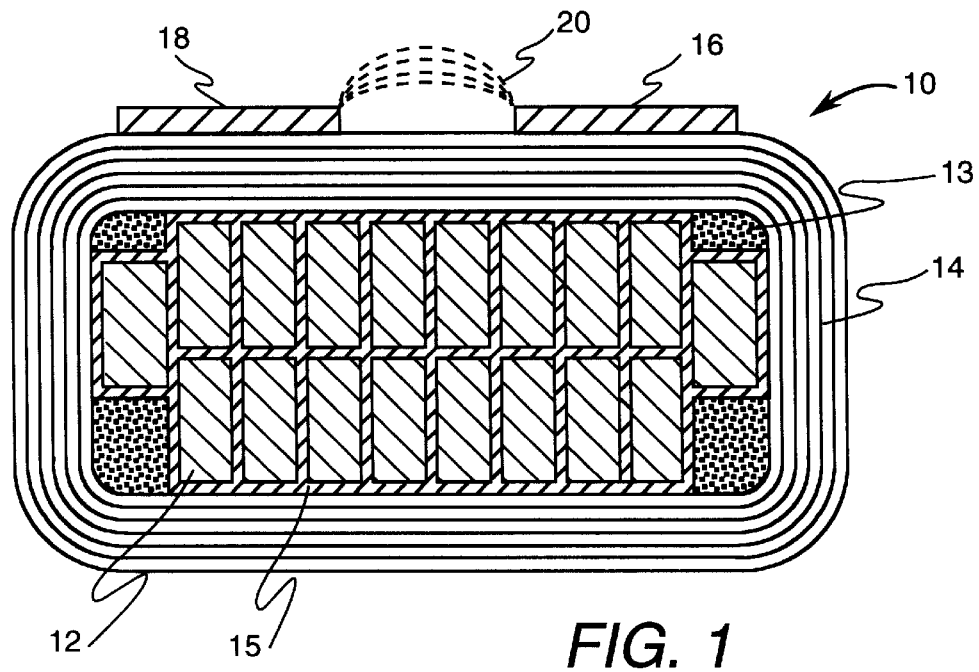
FIG. 1
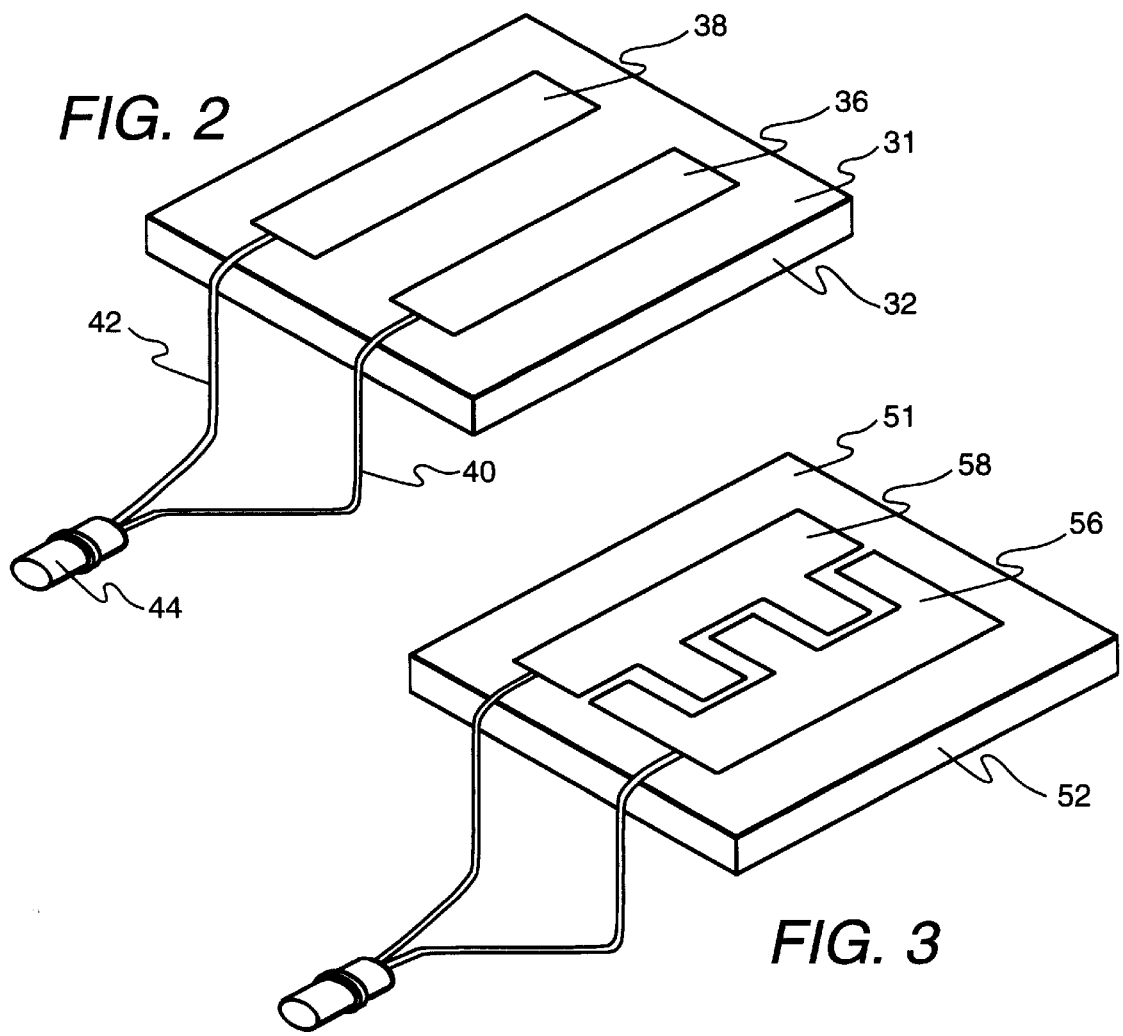
FIG. 2
FIG. 3

METHOD FOR DETERMINING THE PRESENCE OF WATER IN MATERIALS

This invention relates generally to water detection methods. More particularly, it relates to methods for determining the presence of water in insulating materials such as those used in electrical power generation.

BACKGROUND OF THE INVENTION

Water detection methods are available for a variety of end use applications. For example, the water content of porous materials like soil has been measured by using electromagnetic fields, as described in U.S. Pat. No. 5,442,293. Moreover, the determination of moisture content in materials like wet- or cured concrete is sometimes very important in the building industry. U.S. Pat. No. 3,870,951 describes an electrical measuring probe useful for such a purpose.

Water detection is also a critical task when water-cooled electrical generators are employed. The stator yoke in these generators surrounds the armature core and partially encloses the armature windings, which are sometimes referred to as "stator windings" or "stator bars". As one typical example, copper conductors are usually wound in the armature to form loops. The armature windings are arranged in such a manner that the desired voltage and current characteristics can be maintained by the generator in operation. (Current usually flows through the stator in three phases). A number of the individual conductors (sometimes referred to herein as "strands") inside the stator bars are hollow, to allow for the flow of cooling water from a coolant system.

Electrical insulation is wrapped around both the strands and the stator bars, and is also often used to separate some of the strands from each other, or from other conductive structures, e.g., portions of the stator yoke which is usually made of steel. The ground wall insulation which is usually wrapped around the stator bars can be formed of various materials. Examples are fiberglass tape, vacuum/pressure-impregnating resins, casting and potting resins, and different types of laminates made by bonding layers of a reinforcing web.

Mica-based insulating tapes are often used in generators and large motors for a number of reasons. For example, these types of materials provide insulation of high electrical strength and excellent resistance to partial discharges. These materials also perform well in a high temperature environment. Various types of mica-based tapes are available (e.g., Micapal™ tapes). Most of them consist of mica flakes or laminates bound together with a resinous binder, such as an epoxy material. Prior to being cured, the material is flexible enough to be wrapped around a conductive element. When cured, the resulting material is thin and tough.

The durability and integrity of the insulation during operation of electrical generators is of great importance. The stator bars operate at very high voltages, e.g., greater than 10,000 volts in a large generator. The voltage has to remain isolated from ground. Any "flashover" from one stator bar to another, or from one electrical phase to another, could activate safety mechanisms which automatically shut down the generator. A sudden shut-down could instantaneously direct the current flow (often greater than 2,000 amps) to ground—an event which in some circumstances could severely damage many of the generator components.

As those who maintain water-cooled electric generators are well-aware, the leakage of water into the ground-wall insulation can damage it and ultimately lead to the catastrophic failures mentioned above. Water leaks from the coolant system are often found in or near the many brazed connections at the junction of a stator winding terminus and a water hose connection. The leaks are caused by a variety of occurrences, e.g., stress cracks or porosity in copper castings; or corrosion of the braze materials. As described by J. Timperley in *Rotating Machinery*, 62 PAIC 95 (copyright 1995 Doble Engineering Co.), water can then begin migrating along voids between the ground wall insulation and the strands, and can delaminate the mica-flake tape layers within the ground wall insulation. Failure of the generator can occur when water contaminates the ground-wall insulation in the vicinity of the stator core, where higher voltage stresses are present. Although on-line failures of generators due to water leakage are a rare occurrence, the damage caused by such an event could be extreme, as mentioned above.

Failure (i.e., according to test specifications) is most often experienced during routine maintenance or testing of the generator. For example, a stator water pumping unit may be left in operation when the generator is degassed. Under those conditions, the pressure differential may force water through a leak site and into the ground-wall insulation. In general, even very small water leaks can be detrimental to a generator if they are allowed to persist.

There are a number of techniques which are presently used to detect water in electrical insulation. Capacitance mapping is a popular technique, and is described in the Timperley article mentioned above, as well as in other references. In most variations of this technique, an electrode is brought into contact with the insulation, forming a type of capacitor when a DC (direct current) potential is applied across the insulation. As a specific example, a conductive pad could be placed on each stator bar in its end-arm region, and capacitance-to-ground is recorded and compared with readings from adjacent stator bars. The dielectric constant of insulation increases with water content therein, leading to a higher capacitance reading as compared to readings for dry insulation. A plot of the readings can be made, and certain capacitance values or deviations from other values (or from a mean value) can be designated as failures, based on the plot values.

While capacitance mapping is useful in some situations, it also has disadvantages. The technique is often not especially sensitive, with data variations of greater than about 10%. Such a variation requires even larger deviations (e.g., 20%–25%) for particular readings to be meaningful. In such an instance, allowances in regard to the failure-threshold can result in a significant number of passable insulation sections registering as failures. Moreover, thickness variations in the insulation for different stator bars may lead to differences in capacitance measurements for materials having the same water content, or having no water content. This type of variation makes relative comparisons of capacitance readings difficult. Furthermore, the composition of the insulator may adversely affect capacitance mapping. The technique relies on water having a large dielectric constant as compared to the insulating material. However, if the insulator contains inorganic fillers or other constituents, its dielectric constant may be increased to a level closer to that of water, making comparative measurements more difficult.

Perhaps the most serious drawback associated with capacitance mapping is the need for the generator to be off-line when the technique is being used. Usually, the generator must be disconnected from power transmission systems, and the electrical phases must be isolated. The time and labor required in bringing the generator off-line can represent a considerable expense for utility companies or other entities which generate electricity.

One on-line technique for water detection is known as the stator leak monitoring system (SLMS). Such a system relies on a generator arrangement in which the stator is sealed to prevent the entry of air, and is pressurized with hydrogen. The hydrogen pressure is maintained above the pressure of the water in the coolant system. In the event of a water leak, hydrogen will flow into the coolant system and be detected.

Although SLMS can advantageously be employed while the generator is operating, its use is also accompanied by some disadvantages. For example, the technique does not directly measure the presence of water. Instead, it provides an indication that a hydrogen leak is present somewhere, but it does not tell the operator where water leaks may be occurring. It also does not provide an indication that any of the insulation is in fact wet, or where the site of wetness might be.

A direct current technique for detecting water "trees" in insulated power cables has been described by H. Oonishi et al in the literature (IEEE Transactions on Power Delivery, Vol. PWRD-2, No. 1, January 1987). The method involves inserting a probe (which is part of an electrical measuring circuit) into the insulation. The probe is designed to detect any flow of direct current, which in turn serves as an indication of the existence of a water tree.

While the DC technique may be useful in some instances, it also is accompanied with some disadvantages. For example, the probe may not be especially sensitive, because it only detects water which is physically present in the free state on the surface of the probe. Moreover, to be effective, the probe must be physically inserted into the insulation, or encapsulated around it. Such a requirement can cause difficulty if the probe is used for the on-line testing of generators. Moreover, insertion of a probe after the generator has already been installed at a site could compromise the integrity of the insulation.

Other techniques for detecting water links in various settings are also available, e.g., the use of a tracer gas such as sulfur hexafluoride, or the use of thermographic video cameras. However, each technique is characterized by at least one of the disadvantages noted above. The disadvantages can represent special difficulties when the insulation being monitored is part of a high-voltage electrical generator.

Thus, one can readily understand that new methods for detecting the presence of water in materials would be of considerable value. The methods should be capable of accurately detecting water in the surface region of a variety of materials which have an affinity for water molecules. Moreover, these new techniques should be suitable for an insulating material which is incorporated into electrical power equipment, e.g., water-cooled generators. It would be especially beneficial if the techniques could be employed while the power equipment was in operation, so that unnecessary shut-downs could be avoided. Finally, the new methods should be relatively cost-effective, and not add significant expense to any of the related procedures, like power generation.

SUMMARY OF THE INVENTION

In response to the needs discussed above, the present inventors have discovered an improved process for determining the presence of water in a material, comprising the following steps:
(a) placing a set of electrodes on the surface of a layer of a selected material, and establishing an electric field between the electrodes;

(b) measuring the phase angle for the electric field at a pre-selected frequency; and (b) comparing the measured phase angle to a predetermined phase angle for a dry portion of the material, wherein a significant difference between the phase angle for the selected material and the predetermined phase angle for the dry material is indicative of the presence of water in the material.

The process is very useful for monitoring insulating materials for the presence of water, e.g., insulating materials used in electric generators. A key attribute of this invention is that the generators can be in operation, i.e., "on-line", while the presence of water is being monitored.

Since the process is specific to the presence of water, it is not adversely affected by insulation characteristics (e.g., thickness variations), as in the case of capacitance mapping. In some embodiments, multiple sets of electrodes can be used to monitor different sites on the layer of material.

Another embodiment of this invention relates to an electrical generator, comprising:

(i) insulating material surrounding at least a portion of an electrically conductive component in the generator;

(ii) at least one set of electrodes on a surface of the insulating material, said electrodes being connected to a power source which permits the establishment of an electrical field between the electrodes; and (iii) means for measuring a phase angle associated with the electrical field at a selected frequency, wherein the phase angle value for a dry portion of the insulating material exposed to the electrical field is known;

and wherein a comparison of the known phase angle for a dry portion of the insulating material to the measured phase angle for a selected portion of the insulating material will provide an indication of whether water is present in the selected portion of the insulating material.

Other details regarding this invention will follow.

BRIEF DESCRIPTION OF THE DRAWINGS

FIG. 1 is a cross-sectional view of a stator component in a water-cooled electrical generator.

FIG. 2 is top view of a set of electrodes in place on the surface of an insulator layer, according to one embodiment of this invention.

FIG. 3 is top view of a set of electrodes in place on the surface of an insulator layer, according to an alternative embodiment of this invention.

DETAILED DESCRIPTION OF THE INVENTION

Figure 4:
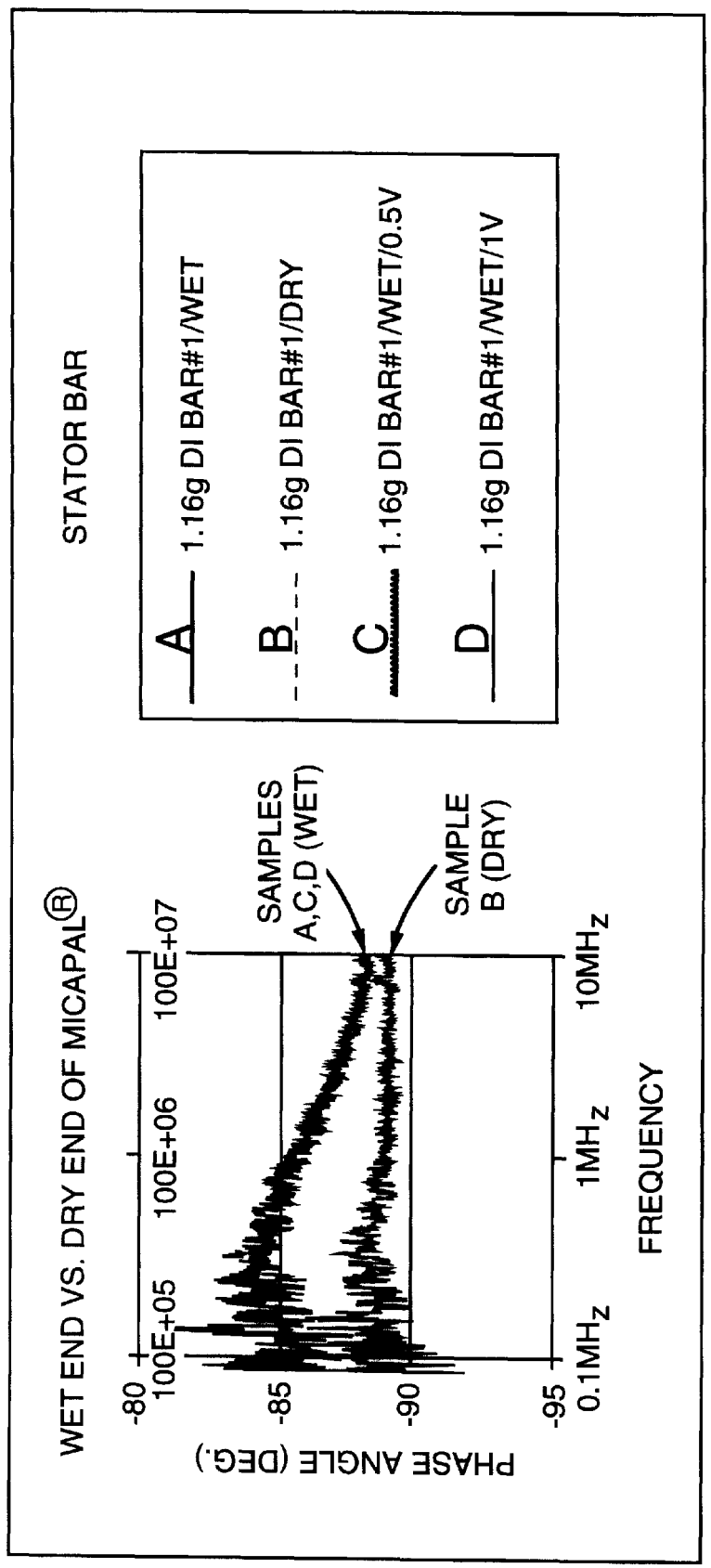
FIG. 4 is a plot of electrical phase angle values as a function of frequency for materials being monitored according to the present invention.

As mentioned above, the method of the present invention can be employed to determine the presence of water in a variety of materials. Suitable materials which can be monitored are those with which water molecules interact. As used herein, "interaction" refers to the cumulative effects of various types of attractive forces which may exist between water and a surface made of the particular material. Examples of these well-known forces, which are much weaker than covalent bonds, are van der Walls' forces, hydrogen bonds, and surface tension forces. The interaction of water molecules with susceptible surfaces will often cause the water to move or "wick" along the surfaces. In this manner, the migrating water may enter openings in the surfaces, leading to problems discussed above, e.g., insulation failure in electrical equipment.

The interaction of water molecules with solid surfaces is discussed in detail in an article entitled "Structure of Water Near Solid Interfaces", Industrial and Engineering Chemistry, Vol. 61, No. 11, November 1969, pp. 10–47, the contents of which are incorporated herein by reference. It is noted in the article that the dielectric properties of water between sheets of mica was investigated. (These dielectric properties are influenced by the behavior of water molecules near a solid surface). Low values for the dielectric constant of water indicated the presence of "oriented" water adjacent to the mica surfaces. Moreover, the dielectric constant of the water decreased with the degree of orientation of the "bound" water layer. Other studies have shown the existence of very firmly bound water at the solid surface or interface, with transition layers extending away from the solid surface, i.e., layers where the water is less firmly bound.

The interaction of water near a solid surface is sometimes considered in terms of the "relaxation" of water molecules near the surface. The concept of intermolecular relaxation and intramolecular relaxation is generally described in various references which are incorporated herein by reference, e.g., the *Kirk-Othmer Encyclopedia of Chemical Technology*, 3rd Edition, Vol. 18, (1982.); and "Motions and Relaxations of Combined Liquids", by S. Granick, *Science*, Vol. 253, September, 1991, pp. 1374–1379. In terms of the present invention, suitable materials for monitoring are those which cause water molecules to exhibit relaxation (i.e., a change in the gain or loss of energy) when the molecules are in the vicinity of the materials.

Non-limiting examples of materials which can be monitored are cellulosic materials like paper; inorganic materials like those based on mica or industrial clays; inorganic oxides, e.g., metal oxides; glass-based materials, e.g., glass fibers; organic polymers; and various combinations of any of these materials. Examples of multi-component materials are mica or glass fiber sheets held together with resinous binder materials. As another example, organic polymers and other base materials are frequently mixed with various fillers or reinforcing agents, such as titanium dioxide, metal carbonates (e.g., calcium carbonate), metal silicates, barium sulfate, and the clays.

Some specific examples of metal oxides are magnesium oxide, aluminum oxide, zinc oxide, and zirconium oxide. Specific examples of organic polymer materials are polyesters, polyamides, polystyrenes which have hydrophilic characteristics (e.g., polyhydroxystyrenes), polyethers, polyimides, silicones (i.e., those which contain water-interactive fillers like aluminum trihydrate); rubber-based polymers; epoxies, phenolics, acrylics, polyurethanes, mixtures of any of the foregoing; and copolymers of any of the foregoing.

There are also examples of materials which would usually not be susceptible to water-monitoring according to this invention. In general, water molecules would not significantly interact (as discussed above) with surfaces formed from such materials. Examples include polytetrafluorethylenes, silicones, and polyethylenes.

The present invention is especially useful for monitoring insulating materials, e.g., thermal insulators and, especially, electrical insulators. Several specific examples of electrical insulation include the mica-based materials discussed above (commercially available under trade names such as Mica-pal™ and Mica-Flex™); alumina-based materials, glass fiber-based materials; and a variety of composite materials, such as those based on laminations of cellulose, glass, asbestos, and/or synthetic fibers, bonded together with resins and then cured. In use, the insulating material is usually in the form of a tape or layer, which can be pre-shaped to surround any component being protected. Multiple layers are sometimes used, e.g., layers of mica-based tape, for a total thickness between about 1 mm and about 10 mm.

FIG. 1 is a cross-sectional view of a typical stator component 10 for a water-cooled electrical generator. The stator includes stationary conductors or strands 12, often made of copper. The strands in the central portion of the figure are electrically-insulated from each other by an enamel material 15, while the strands at each end are surrounded by transposition putty material 13. For this type of generator, some of the strands 12 are hollow, to allow the passage of water to and from the coolant system, as described above. (Electrical generators are well-known in the art and described in many references).

The strands 12 are surrounded by multiple layers of electrical insulation 14, i.e., ground wall insulation. The number of insulation layers and their particular arrangement are not critical, and depend on design specifications for the generator. Often, the insulation layers are made from mica-based materials which include a binder, as mentioned previously. After curing, the mica layers are relatively hard, but flexible enough to be wound or wrapped around the strands then cured to hardness.

Electrodes 16 and 18 are placed on an outside surface of insulation 14. The shape and size of the electrodes are not critical to this invention, as long as an electric field 20 (illustrated in phantom) can be generated between them. A particular voltage for the electrical field is also not especially important, and depends in part on which voltage measurements will allow for the most convenient readings of phase angle and frequency, as further discussed below. In general, the voltage is usually in the range of about 100 millivolts to about 2 volts, and more frequently, between about 0.5 volt and 1 volt.

FIG. 2 is top view of a set of electrodes 36, 38 in place on the surface 31 of an insulator 32, which could represent one or more of the insulator layers depicted in FIG. 1. In this embodiment, each electrode is substantially rectangular, and parallel to each other. The length and thickness of the electrodes are not particularly critical, and are dictated in part by the durability of the electrode material and the size of the material being monitored. The electrodes can be made from any conductive material, such as metals or metal alloys, or conductive polymers. Examples of suitable metals are copper, aluminum, steel (e.g., stainless steel), iron, and tin, with copper being preferred in some embodiments.

Examples of the conductive polymers are doped polytetrafluoroethylene, polyvinyl carbazole, ferrocene-based polymers, and silicones or other organic resins which contain electrically-conductive additives. Polymeric electrodes (which can be cured after being applied to a surface) are sometimes preferred for rough substrates, because of their ability to closely conform to such a surface. Electrodes made of materials like polytetrafluoroethylene may also be preferred in dusty or unclean areas, because they would be relatively easy to clean.

The separation between the electrodes will depend in part on the thickness of the material being monitored. A greater separation allows for greater penetration of the electric field into the depth of the material, although the strength of the field may have to be increased to achieve desired sensitivity within the ranges discussed above. In general, the distance between the electrodes will range from about 0.1 cm to about 2.0 cm, and usually, from about 0.5 cm to about 1.5 cm. For a layer of material having a thickness of about 0.4 cm to about 0.8 cm, the distance between the electrodes is usually in the range of about 0.8 cm to about 1.2 cm.

Each electrode can be attached to a wire or lead 40, 42. The leads may in turn be fitted into a connector, e.g., a BNC fitting, and then routed to an appropriate power supply. The power supply is usually part of a phase analyzer device, as described below.

FIG. 3 is top view of an alternative set of electrodes 56, 58 in place on the surface 51 of an insulator layer 52. In this embodiment, the electrodes are still separated from each other, but interdigitated. Such an arrangement is preferred in some embodiments because it permits the establishment of an electric field over a greater amount of surface area in a particular section of the material being monitored. The spacing for this set of electrodes will be as described above. Moreover, other arrangements of electrodes are also possible. For example, they could be situated in a concentric arrangement, which would also permit the monitoring of a considerable surface area of material. Those skilled in the art will be able to readily evaluate different arrangements for the electrodes for a given type and shape of material being examined for water content, based on the teachings herein.

If necessary for stability, the electrodes could be affixed to the surface of the material being monitored. Any technique could be used to affix the electrodes, as long as it did not interfere with their ability to contain the electric field. Examples include the use of adhesives, an air pressure pad, or mechanical means, e.g., brackets. The electrodes should be easily detachable from the surface if their position on the surface is to be frequently changed.

The electrical phase angle is a known measurement for an electric field having a given frequency. Phase analyzers are commercially available from various manufacturers, such as Hewlett-Packard. The phase analyzer can easily be connected to the electrodes through the BNC fitting.

The most appropriate frequency for carrying out this invention is that which is most sensitive to the presence of water in a particular material being monitored. It can be determined without undue effort by testing trial samples of the material. Usually, the frequency at which the phase angle will be measured is in the range of about 1 MHz to about 3 MHz, but it could extend to as low as about 10 KHz, or as high as about 100 MHz.

When the most appropriate frequency has been established, the phase angle can be measured for a material free of water, at that particular frequency. A significant change in that phase angle value for a test material will indicate the presence of water in the test material, due in part to the change in relaxation time for water molecules within the material being monitored. As the water content increases, the strength of the "relaxation signal" may also increase, as evidenced by a greater change in the phase angle value.

A "significant change" in the phase angle will depend in part on the type of material being monitored, and the depth of water within a layer of the material. Usually, a variation of phase angle of about 0.3 degrees or more (i.e., a variation from the phase angle value for the material in its dry state) is a reliable indication that water is present in the material. As an illustration, a typical phase angle value (within the frequency range stated above) for a dry portion of an inorganic-based insulating material is often about (minus) −89.5 degrees. A reading of −89.4 or −89.3 degrees for a test sample of the material is still considered to be indicative of a dry material, while a reading of about −89.2 degrees is a good indication that water may be present in the sample. Readings of less than about −89.2 degrees reliably confirm the presence of water. (There may sometimes be slight variations for phase angle values for a given sample, due in part to minor electrical fluctuations related to the equipment being used. However, the average of repeated readings confirms that any deviation is usually insignificant).

The present process can be used to detect water to a depth of up to about 1.5 cm within a layer (or through multiple layers) of material, such as mica- or cellulose-based insulation. Usually, the depth at which water is detected is in the range of about 0.5 cm to about 1.0 cm. As mentioned above, the spacing of the electrodes, as well as the strength of the electric field, can be varied to test for water at different depths. Usually, if the water content increases at a given depth, the phase angle value exhibits a greater change, as discussed above. If the water content remains constant, but its depth within the layer of material increases, the relaxation signal tends to decrease, as signified by a smaller change in the phase angle value.

Sometimes, the most appropriate electrical frequency to be used for testing a given type of material is not known. In that instance, it can be determined by carrying out a frequency sweep for the electrical field established between the electrodes. The frequency sweep establishes a plot of the electrical phase angle as a function of the frequency being generated. It can readily be measured by the use of a device which measures these types of field properties, such as an impedance/gain-phase analyzer. In the examples which follow, a frequency sweep is undertaken as the sample is tested for the presence of water.

It should be apparent that the presently-described process would be very useful for monitoring the presence of water in or around electrical components, such as electrical generators. In view of the fact that direct current and alternating-current (AC) generators are well-known, an extensive description of them is not necessary here. (See, for example, the Encyclopedia Americana, International Edition, Volume 12, copyright 1964, pp. 378–385, the contents of which are incorporated herein by reference). The primary components of a DC generator are the armature, the field poles, brushes, brush rigging, commutator, frame (or "yoke"), and end frames or end bells. In an AC generator, the stationary conductors (armature coils) are held in place in slots in a frame assembly (stator), as alluded to earlier. The assembly that supports the field coils and rotating poles is referred to as the "rotor".

Insulating materials may sometimes be used to separate or encapsulate the principal components mentioned above, as well as various other components, such as interpoles, compensating windings, and devices or controls which regulate the generated voltage and current output. Water from any outside source which seeps into the insulation or penetrates it in some other manner may be of great concern. Moreover, water which originates in the cooling system of a water-cooled generator and migrates into the insulation (as described previously) can also represent a serious problem. The process described herein effectively addresses these concerns. (The present invention can be used to detect the presence of deionized water, which is often used for cooling systems, or regular tap water).

Thus, another embodiment of this invention is directed to an electrical generator, comprising;

(i) insulating material surrounding at least a portion of an electrically conductive component in the generator;

(ii) at least one set of electrodes on a surface of the insulating material, said electrodes being connected to a power source which permits the establishment of an electrical field between the electrodes; and (iii) means for measuring a phase angle associated with the electrical field at a selected frequency, wherein the phase angle value for a dry portion of the insulating material exposed to the electrical field is known;

and wherein a comparison of the known phase angle for a dry portion of the insulating material to the measured phase angle for a selected portion of the insulating material will provide an indication of whether water is present in the selected portion of the insulating material.

Multiple sets of electrodes could be placed on the surface of the insulating material, e.g., on the surface of insulating material which surrounds stator bars in a water-cooled generator. Each set of electrodes could be connected to its own power source and phase analyzer. Alternatively, all of the sets could be connected to a central power source and phase analyzer, via a circuit pathway which could be readily designed by those skilled in the art. In this manner, many different sites on the insulation can be simultaneously monitored for the presence of water. An additional attribute of this invention is that the presence of electrical conductors (e.g., copper windings) in the vicinity of the electrodes and the electrical field does not adversely affect phase angle measurements for the process.

EXAMPLES

This example is merely illustrative, and should not be construed to be any sort of limitation on the scope of the claimed invention.

Two copper strips, each having dimensions (thickness, width, length) of 0.076 mm×5 mm×50 mm, were used as electrodes in this experiment. The strips were placed in a position parallel to each other (along their length) on a surface of a portion of insulation consisting of about 10–12 successive layers of mica-based tape, having a total thickness of about 3–4 mm. (The mica tapes had been resin-bonded to each other).

The spacing between the electrodes was about 8 mm, and they were affixed to the surface of the mica material with an adhesive. Each strip was connected with leads to a BNC fitting. The BNC fitting was in turn connected to an HP4194A impedance/gain-phase analyzer with an HP54003 50 Ohm impedance probe. The phase analyzer had a frequency range of 10 kHz–50 MHz.

Four samples of the mica-based material were used. Samples A, C and D were saturated with water, while sample B was dry.

For each sample, an electric field was established between the electrodes. The strength of the electric field for samples A–C was 0.5V, while the strength of the field for sample D was 1V. In each instance, the phase angle value at a frequency of about 2 MHz was measured and recorded.

FIG. 4 is a plot of electrical phase angle values as a function of frequency for samples A–D. Sample B, which contained no water, had a phase angle value of about –89.5 degrees. Samples A, C and D each had a phase angle of about –87.0 degrees, clearly indicating the presence of water.

Additional experiments verified the reproducibility of the results, and also demonstrated that moisture in the vicinity of the interface between the insulating material and an electrical conductor could be detected.

The preferred embodiments have been set forth herein for the purpose of illustration. However, this description should not be deemed to be a limitation on the scope of the invention. Accordingly, various modifications, adaptations, and alternatives may occur to one skilled in the art without departing from the spirit and scope of the claimed inventive concept.

All of the patents, patent applications, articles, and texts which are mentioned above are incorporated herein by reference.

What is claimed:

1. A method for determining the presence of water in a selected material, comprising the following steps:

(a) establishing an electric field between at least one set of electrodes on a surface of the selected material;

(b) measuring the phase angle for the electric field at a pre-selected frequency in a range between about 0.01 MHz and about 100 MHz; and (c) comparing the measured phase angle to a phase angle measured at the pre-selected frequency for a dry portion of the material, wherein a significant difference between the phase angle for the selected material and the phase angle measured at the pre-selected frequency for a dry portion of the material is indicative of the presence of water in the selected material.

2. The method of claim 1, wherein each electrode is substantially rectangular in shape, and parallel to the other electrode.

3. The method of claim 1, wherein the distance between the electrodes is in the range of about 0.1 cm to about 2 cm.

4. The method of claim 1, wherein the electrodes are interdigitated.

5. The method of claim 1, wherein the electric field is established at a voltage in the range of about 100 millivolts to about 2 volts.

6. The method of claim 1, wherein the electrodes are formed from a conductive material selected from the group consisting of metals, metal alloys, and conductive polymers.

7. The method of claim 6, wherein the metal is selected from the group consisting of copper, aluminum, iron, tin, and steel.

8. The method of claim 1, wherein the difference in the phase angle for an insulating material in which water is present is at least about 0.3 degrees from the phase angle for an insulating material in which water is not present.

9. The method of claim 1, wherein water is detected in the selected material at a total depth of up to about 1.5 cm.

10. The method of claim 1, wherein the selected material is one which causes water molecules to exhibit relaxation when the molecules are in the vicinity of the material.

11. The method of claim 10, wherein the selected material is an electrical-insulating material.

12. The method of claim 11, wherein the insulating material comprises at least one constituent selected from the group consisting of paper, cellulosic material, organic polymers, glass, inorganic oxides, and combinations of any of the foregoing.

13. The method of claim 12, wherein the insulating material further comprises a binder.

14. The method of claim 12, wherein the insulating material further comprises at least one filler or reinforcing agent.

15. The method of claim 12, wherein the organic polymer is selected from the group consisting of polyesters, polyamides, polyethers, polyimides, carbon-containing silicones, rubber-based polymers; epoxies, phenolics, acrylics, polyurethanes, mixtures of any of the foregoing; and copolymers of any of the foregoing.

16. The method of claim 12, wherein the inorganic oxide is a metal oxide.

17. The method of claim 11, wherein the insulating material comprises mica and a binder.

18. The method of claim 17, wherein the binder comprises an epoxy.

19. The method of claim 1, wherein step (b) further comprises carrying out a frequency sweep for the electric field, to establish a plot of the phase angle as a function of the frequency being generated for the field.

20. The method of claim 19, wherein the frequency sweep is carried out by using an impedance/gain-phase analyzer.

21. A method according to claim 1 wherein the phase angle for the electric field is measured at a pre-selected frequency in a range between about 0.075 MHz and about 5 MHz.

22. A method according to claim 1 wherein the phase angle for the electric field is measured at a pre-selected frequency in a range between about 1 MHz and about 3 MHz.

23. A method for determining the presence of water within insulating material in a water-cooled electrical generator, comprising the following steps:
   (a) placing at least one set of electrodes on the surface of the insulating material, and establishing an electric field between the electrodes;
   (b) measuring the phase angle for the electric field at a pre-selected frequency in a range between about 0.01 MHz and about 100 MHz; and
   (c) comparing the measured phase angle to a phase angle measured at the pre-selected frequency for a dry portion of the material, wherein a significant difference between the phase angle for the selected material and the phase angle measured at the pre-selected frequency for a dry Portion of the material is indicative of the presence of water in the selected material.

24. The method of claim 23, wherein at least a portion of the insulating material surrounds stator components in the generator.

25. The method of claim 23, wherein the electrical generator is in operation while the presence of water is being determined.

26. The method of claim 23, wherein the insulating material comprises mica.

27. A method according to claim 23 wherein the phase angle for the electric field is measured at a pre-selected frequency in a range between about 0.075 MHz and about 5 MHz.

28. A method according to claim 23 wherein the phase angle for the electric field is measured at a pre-select frequency in a range between about 1 MHz and about 3 MHz.

29. An electrical generator, comprising:
   (i) insulating material surrounding at least a portion of an electrically conductive component in the generator;
   (ii) at least one set of electrodes on a surface of the insulating material, said electrodes being connected to a power source which permits the establishment of an electrical field between the electrodes; and
   (iii) means for measuring a phase angle associated with the electrical field at a selected frequency in a range between about 0.01 MHz and about 100 MHz, wherein the phase angle value for a dry portion of the insulating material exposed to the electrical field is known;

and wherein a comparison of the known phase angle for a dry portion of the insulating material to the measured phase angle for a selected portion of the insulating material will provide an indication of whether water is present in the selected portion of the insulating material.

30. A water-cooled electrical generator according to claim 29, comprising a stator bar which includes strands, wherein at least a portion of the insulating material on which the set of electrodes is placed surrounds at least a portion of the stator bar.

31. The electrical generator of claim 30, wherein at least a portion of the insulating material is mica-based.

32. An electrical generator according to claim 29 wherein the means for measuring a phase angle associated with the electrical field at a selected frequency in a range between about 0.075 MHz and about 5 MHz.

33. An electrical generator according to claim 29 wherein the means for measuring a phase angle associated with the electrical field at a selected frequency in a range between about 1 MHz and about 3 MHz.

* * * * *